US00PP23139P3

(12) United States Plant Patent

Klemm et al.

(10) Patent No.: US PP23,139 P3

(45) Date of Patent: Oct. 23, 2012

(54) *OSTEOSPERMUM* PLANT NAMED 'KLEOE10178'

(50) Latin Name: *Osteospermum ecklonis* Norl.
Varietal Denomination: KLEOE10178

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 28 days.

(21) Appl. No.: 13/065,547

(22) Filed: Mar. 24, 2011

(65) Prior Publication Data

US 2012/0246784 P1 Sep. 27, 2012

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt

(74) *Attorney, Agent, or Firm* — Jondle & Associates, P.C.

(57) ABSTRACT

An *Osteospermum* variety named 'KLEOE10178' particularly distinguished by soft pink flowers with creamy white eyes, and a medium compact, slim and upright growth habit, is disclosed.

1 Drawing Sheet

Genus and species: *Osteospermum ecklonis* Norl.
Variety denomination: 'KLEOE10178'.

BACKGROUND OF THE NEW PLANT

The present invention comprises a new and distinct variety of *Osteospermum,* botanically known as *Osteospermum ecklonis* Norl., and hereinafter referred to by the variety name 'KLEOE10178'. The new variety originated from an open pollination made in August 2007 in Stuttgart, Germany. Neither the female parent nor the male parent is known. A single plant selection was subsequently chosen for further evaluation and for asexual propagation.

The new variety was first propagated via vegetative cuttings in May 2008 in Stuttgart, Germany and has been asexually reproduced repeatedly by vegetative cuttings over three to four generations. The present invention has been found to retain its distinctive characteristics through successive asexual propagations via vegetative cuttings.

Plant Breeder's Rights for this variety were applied for in Canada on Mar. 19, 2010. 'KLEOE10178' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Soft pink flowers with creamy white eyes; and
2. Medium compact, slim and upright growth habit.

DESCRIPTION OF THE PHOTOGRAPH

This new *Osteospermum* plant is illustrated by the accompanying photograph which shows a close-up of a flower of the plant. The colors shown are as true as can be reasonably obtained by conventional photographic procedures. The photograph was taken in Summer 2010 of a 7-month old plant in the field in Stuttgart, Germany, under conditions which approximate those generally used in normal horticultural practice.

DESCRIPTION OF THE NEW VARIETY

The following detailed descriptions set forth the distinctive characteristics of 'KLEOE10178'. The data which define these characteristics were collected from asexual reproductions carried out in Stuttgart, Germany. The plant history was taken in the Summer of 2010 on 7-month old plants which were potted at 4 weeks in 12 centimeter containers and then planted in the ground in May 2010. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:

*Family.*—Asteraceae.

*Botanical name.*—*Osteospermum ecklonis* Norl.

*Common name.*—African daisy.

Plant:

*Form and habit.*—Herbaceous perennial but usually cultivated as an annual.

*Growth habit.*—Upright.

*Branching habit.*—Freely branching.

*Height* (*from top of soil, including inflorescence*).—30.0 cm.

*Width* (*including inflorescences*).—24.0 cm.

*Propagation.*—Vegetative cuttings.

*Time to produce a finished flowering plant.*—Approximately 14 weeks from sticking.

*Time to initiate and develop roots.*—Approximately 3 weeks.

*Root description.*—Freely rooting.

Leaves:
*Arrangement.*—Alternate.
*Shape.*—Dentiform.
*Apex.*—Obtuse.
*Base.*—Acute.
*Margin.*—Serrate.
*Color.*—Immature leaf: Upper surface: RHS 137B. Lower surface: RHS 146B. Mature leaf: Upper surface: RHS N137A. Lower surface: RHS N147B.
*Length.*—6.5 cm.
*Width.*—3.5 cm.
*Texture.*—Leathery.
*Petioles.*—Absent.

Stems:
*Total number of branches at base of plant.*—6.
*Length.*—26.0 cm.
*Diameter.*—0.4 cm.
*Internode length.*—1.2 cm.
*Color.*—RHS 143C.
*Texture.*—Rough.

Inflorescence buds:
*Shape.*—Obovate.
*Length.*—0.9 cm.
*Diameter.*—1.2 cm.

Inflorescence:
*Type.*—Single.
*Blooming habit.*—Spring to Fall.
*Quantity of inflorescences per plant.*—Approximately 20.
*Lastingness of the inflorescences on the plant.*—Approximately 14 days.
*Fragrance.*—Absent.
*Inflorescence diameter.*—Approximately 6.5 cm.
*Disc diameter.*—Approximately 1.5 cm.

Disc floret:
*Quantity per inflorescence.*—Approximately 50.
*Shape.*—Oblanceolate.
*Tube color.*—Closed: RHS 12D at base and RHS 11D at top. Mature: RHS 8D.
*Length.*—Approximately 0.5 cm.
*Diameter* (*at apex*).—Approximately 0.2 cm.
*Apex.*—Obtuse.
*Apex color.*—RHS N87A.
*Base.*—Acute.
*Margin.*—Entire.

Ray floret:
*Quantity per inflorescence.*—Approximately 22.
*Shape.*—Oblanceolate.
*Color.*—Upper surface: RHS 75A on top and RHS NN155D on bottom. Lower surface: RHS 162C on top and RHS 158B on bottom.
*Length.*—Approximately 4.0 cm.
*Width.*—Approximately 0.9 cm.
*Apex.*—Obtuse.
*Base.*—Acute.
*Margin.*—Entire.
*Texture.*—Smooth.
*Peduncle.*—Length: Approximately 7.0 cm. Diameter: Approximately 0.2 cm. Texture: Rough. Color: RHS 138A.

Phyllaries:
*Arrangement.*—Single.
*Observed quantity per plant.*—Approximately 20.
*Shape.*—Lanceolate.
*Color.*—Upper surface: RHS 138A. Lower surface: RHS 139C.
*Length.*—Approximately 1.2 cm.
*Width.*—Approximately 0.15 cm.
*Apex.*—Acute.
*Base.*—Obtuse.
*Margin.*—Entire.
*Texture.*—Rough.

Reproductive organs:
*Androecium.*—Location: Located at the base of the disc floret corolla. Stamens: Quantity: Approximately 50. Shape: Filamentous. Color: RHS N81D. Filament length: Approximately 0.45 cm. Filament diameter: Approximately 0.012 cm. Anther: Shape: Elliptic. Color: RHS N79A. Length: 0.25 cm. Diameter: 0.05 cm. Pollen: Color: RHS 25A. Amount: Abundant.
*Gynoecium.*—Location: Located at the base of the petals (ray floret); pistils in disc flower are degenerated and not functional. Pistils: Number: Approximately 22. Length: 0.6 cm. Diameter: 0.12 cm. Stigma: Color: RHS N155B in the center and RHS N79A at the edge. Shape: Bipartite. Length: Approximately 0.2 cm. Diameter: Approximately 0.05 cm. Style: Color: RHS N155B. Length: Approximately 3.0 cm. Diameter: Approximately 0.02 cm. Shape: Elliptic.

Fruit and seed set: Seed set was observed.

COMPARISON WITH COMMERCIAL VARIETY

'KLEOE10178' differs from the commercial cultivar 'FlowerPower Light Pink' (unpatented) in that 'KLEOE10178' has medium-sized, soft pink flowers with creamy white eyes, while 'FlowerPower Light Pink' has large-sized, dark pink flowers with light pink eyes. In addition, 'KLEOE10178' has a medium compact, slim and upright growth habit, while 'FlowerPower Light Pink' has a very compact, round growth habit.

We claim:

1. A new and distinct variety of *Osteospermum* plant named 'KLEOE10178' as shown and described herein.

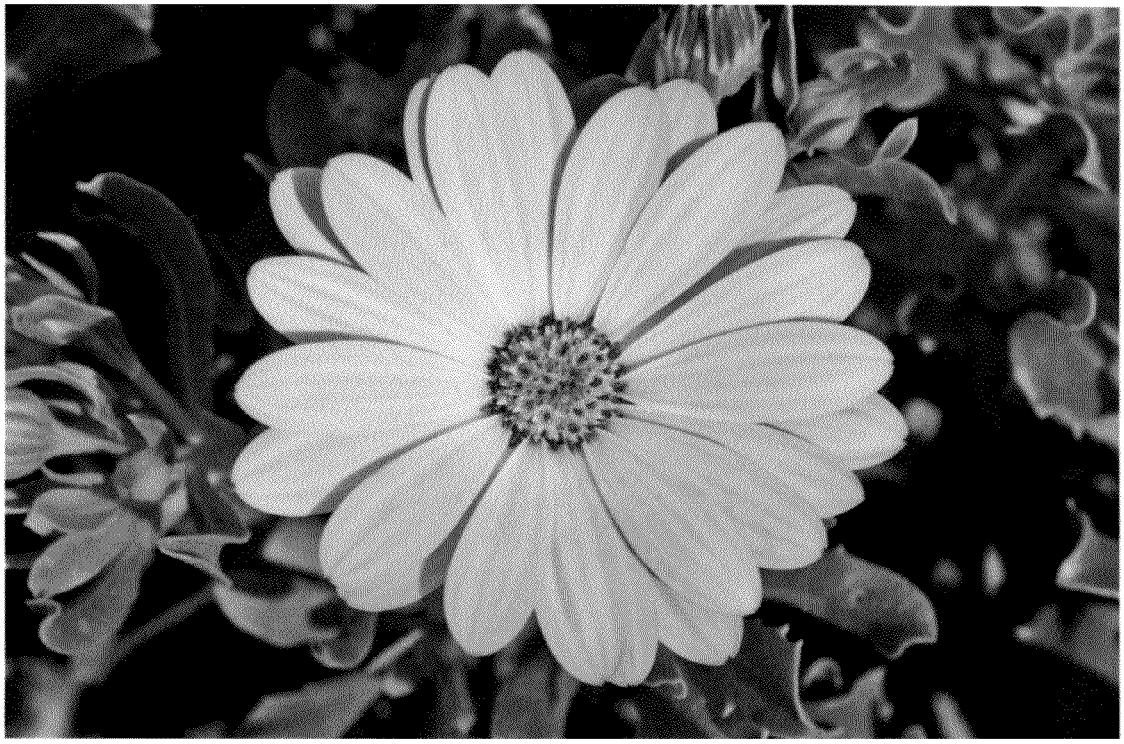

* * * * *